United States Patent
Stone

[19]

[11] Patent Number: 6,126,832
[45] Date of Patent: *Oct. 3, 2000

[54] COMPOSITION FOR DIALYSIS AND SHOCK TREATMENT

[76] Inventor: Andrew Stone, 5818 NW. 34 Way, Boca Raton, Fla. 33946

[*] Notice: This patent issued on a continued prosecution application filed under 37 CFR 1.53(d), and is subject to the twenty year patent term provisions of 35 U.S.C. 154(a)(2).

[21] Appl. No.: 08/961,658

[22] Filed: Oct. 31, 1997

Related U.S. Application Data

[63] Continuation-in-part of application No. 08/797,695, Jan. 31, 1997, Pat. No. 5,755,968, which is a continuation-in-part of application No. 08/225,894, Apr. 11, 1994, Pat. No. 5,620,604, which is a continuation-in-part of application No. 07/922,673, Jul. 30, 1992, abandoned.

[51] Int. Cl.[7] ..................................................... A61K 38/01
[52] U.S. Cl. .............................. 210/647; 210/646; 514/2; 514/58
[58] Field of Search ..................................... 210/646, 647; 604/29; 514/2, 58, 929; 424/646, 663, 677, 717

[56] References Cited

U.S. PATENT DOCUMENTS

| | | |
|---|---|---|
| 3,669,880 | 6/1972 | Marantz et al. .................... 210/647 |
| 4,133,891 | 1/1979 | Nolph .................................. 424/295 |
| 4,761,237 | 8/1988 | Alexander et al. .................. 210/647 |
| 4,886,789 | 12/1989 | Milner ................................ 210/647 |
| 4,889,634 | 12/1989 | El-Rashidy ........................ 210/646 |
| 4,906,616 | 3/1990 | Gilchrist et al. ........................ 514/2 |
| 5,039,609 | 8/1991 | Klein .................................. 530/414 |
| 5,108,767 | 4/1992 | Mulchandani et al. ................ 514/2 |
| 5,578,576 | 11/1996 | Leddin ................................ 514/21 |
| 5,631,025 | 5/1997 | Shockley et al. .................... 514/23 |

*Primary Examiner*—John Kim
*Attorney, Agent, or Firm*—Robert D. Katz; Peter J. Phillips

[57] ABSTRACT

A dialysis system and method for removing toxic matter from the large intestine comprises an input tube, an output tube concentric with the input tube, both of which tubes are to be inserted in the large intestine an input pressure pump connected to deliver filtrate solution from an input container to the input tube, and an output suction pump connected to the output tube to remove filtrate solution. Pressure gauges control the input and output pumps so that an input pressure level of 75 mm Hg is not exceeded, and so that the output suction pump is disabled unless the input pressure level exceeds 45 mm Hg. A filtrate solution composition comprising a vasodilator of niacin, a high molecular weight protein in the form of casein, a mineral constituents and other components is also provided. The composition may be formed of electrolytes, buffers and a high molecular weight osmotic agent. The system and method may be adapted to treat shock. A shock treatment composition may comprise electrolytes, buffers and a rehydrating agent.

20 Claims, 3 Drawing Sheets

COMPOSITION FOR DIALYSIS AND SHOCK TREATMENT

CROSS-REFERENCE TO RELATED APPLICATIONS

This application is a continuation-in-part of application Ser. No. 08/797,695, filed Jan. 31, 1997, now U.S. Pat. No. 5,755,968, which is a continuation-in-part of application Ser. No. 08/225,894, filed Apr. 11, 1994, U.S. Pat. No. 5,620,604, which is a continuation-in-part of application Ser. No. 07/922,673, filed Jul. 30, 1992, abandoned.

BACKGROUND OF THE INVENTION

The present invention is directed to a dialysis system, method and composition especially useful for removing toxic matter from the serum of the large intestine, and to a system, method and composition for shock treatment.

SUMMARY OF THE INVENTION

It is an object of the present invention to replace normal hemodialysis in the filtration of toxic substances in the serum.

It is another object of the present invention to provide a dialysis system and method for a patient which will result in substantially no blood loss during dialysis treatment.

It is yet another objection of the present invention to provide a dialysis system and method which substantially eliminates the risk of infection.

It is a further object of the present invention to provide a dialysis system and method using components which are relatively low in cost so that each patient should be able to afford his or her own individual system, which will further allow for increased time available for dialysis, therefore increasing treatment proficiency, and also reduce or substantially eliminate the risk of cross infection.

It is a yet further object of the present invention to provide a dialysis system and method having components which are of simple design and easy to use, thereby obviating the need for specially trained medical technicians.

It is a yet further object of the present invention to provide a system, method and composition for treating shock.

In accordance with the present invention, a dialysis system for removing toxic matter from the serum of the large intestine is provided, comprising means for introducing a dialysis filtrate solution to the large intestine of a patient at a first location, said filtrate providing a vehicle for removing toxic matter from the serum of the large intestine, said means for introducing comprising a flexible input tube having a distal end for insertion into the large intestine and having a first inflatable balloon at the distal end of said input tube, means for removing waste filtrate from the large intestine at a second location spaced from the first location after the filtrate removes toxic matter from the serum, said means for removing comprising a flexible output tube having a distal end for insertion into the large intestine and having a second inflatable balloon at the distal end of said output tube, said first and second balloons being spaced from each other for sealing off a portion of the descending colon of the large intestine, a third inflatable balloon between said first and second inflatable balloons, and means for providing fluid to said first, second and third inflatable balloons to thereby inflate said balloons, said means for providing fluid being independent from said means for introducing a dialysis filtrate solution.

The invention also provides a dialysis method for removing toxic matter from the serum of the large intestine of a patient, comprising the steps of introducing into the large intestine of a patient a tube having a distal end with first and second inflatable balloons spaced from each other at the distal end thereof, and a third inflatable balloon between the first and second inflatable balloons, inflating the first and second inflatable balloons, to seal off a portion of the large intestine of the patient, and the third inflatable balloon, introducing a dialysis filtrate solution to the large intestine of the patient from the third inflatable balloon at a first location adjacent the first inflatable balloon independently after said inflating step, said dialysis filtrate solution providing a vehicle for removing toxic matter from the serum of the large intestine, and removing waste filtrate from the large intestine through the third inflatable balloon at a second location which is spaced from the first location and adjacent the second inflatable balloon to remove toxic matter from the serum between the first location and second location.

The invention also provides a system and method for treating shock.

The invention also provides a filtrate composition for use in dialysis, comprising a vasodilator, a high molecular weight protein to effect osmotic pressure to achieve diffusion of element across the large intestine membrane into the filtrate, and mineral constituents for maintaining proper serum levels in the large intestine.

The dialysis filtrate composition may comprise electrolyte ingredients, buffers and a high molecular weight osmotic agent for removing nitrogenous waste.

The invention also provides a system and method for treating shock, which can be adapted from the same system and method for dialysis. The composition for treating shock may comprise electrolyte ingredients, buffers and a rehydrating agent.

DETAILED DESCRIPTION OF THE PREFERRED EMBODIMENT

Figure 1:
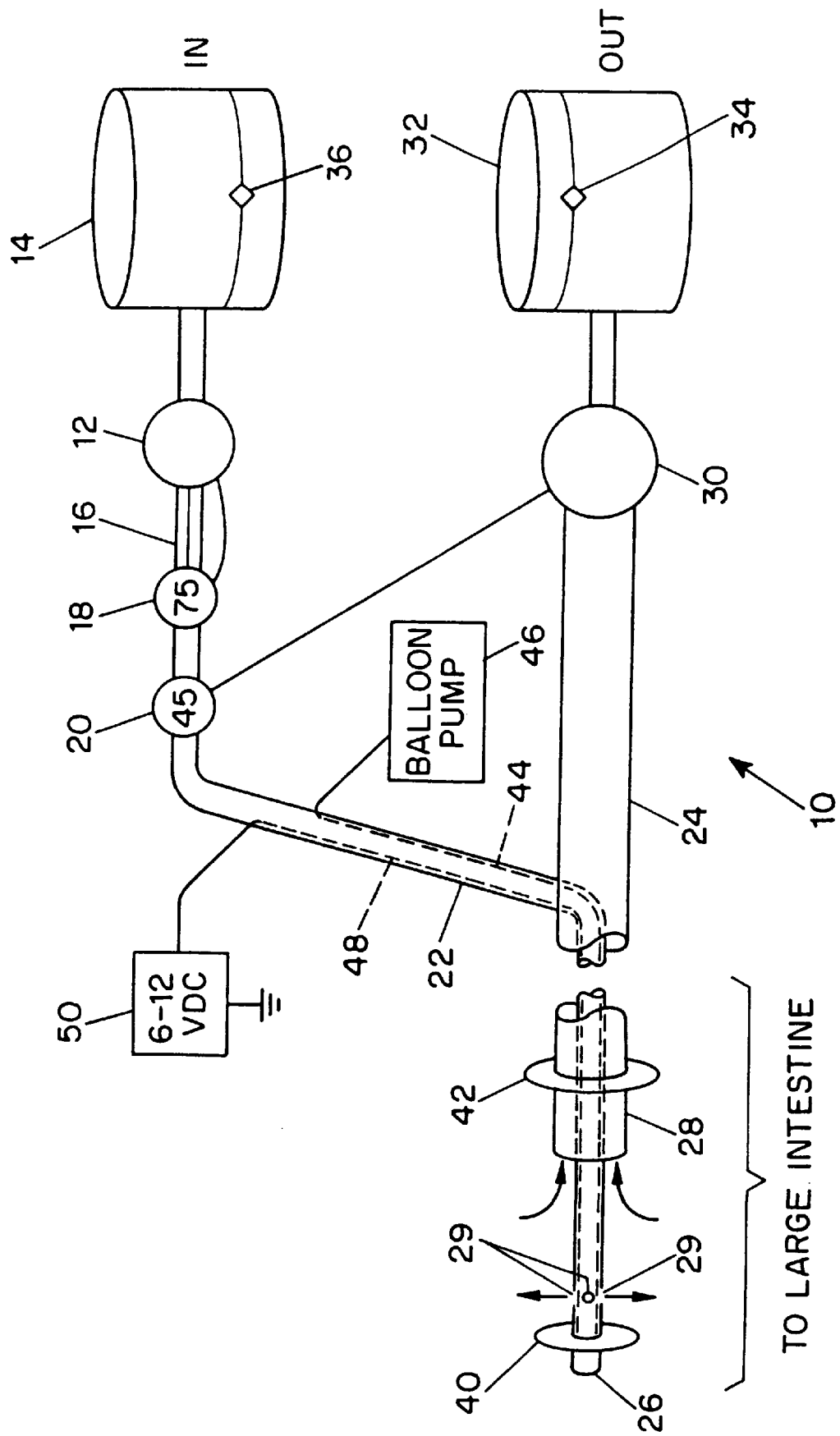
FIG. 1 is a block diagram of a system according to the present invention.

As shown in FIG. 1, the dialysis system 10 according to the present invention comprises an input pump 12 connected to an input dialysis solution container 14. The input pump 12 has its output 16 connected in line with two pressure gauges, the first one being a 75 mm Hg pressure gauge 18 and the second one being a 45 mm Hg pressure gauge 20. To the output of input pump 12 is connected a flexible plastic input tube 22 which is fed through the sidewall of an output tube 24 also being made of flexible plastic. The input and output tubes 22, 24 are concentric, with the input tube having a distal end 26 about 14–22 inches longer than the distal end 28 of the output tube 24. The differential in the lengths of the two tubes will be determined according to patient size, and of course may be outside of this range. Adjacent the distal end 26 of the input tube are a plurality of openings 29 for introducing the dialysis fluid into the large intestine at a first location. The fluid is removed at a second location as shown by the arrow at the distal end 28 of the output tube 24.

Also shown in the FIG. 1 is an output suction pump 30 connected to an output container 32. The output container 32 has a capacity of about 8 liters and has a float switch 34 to detect when the level of fluid in the output container 32 is greater than about 105% of its capacity, i.e. about 8.4 liters. When the float switch 34 detects that the fluid level exceeds 8.4 liters, the output pump 30 is disabled or de-energized. This action guards against the patient becoming dehydrated. However, if the patient does become dehydrated, he or she may have to drink a small quantity of water or juice to return to normal osmotic balance.

The capacity of the input container 14 is also about 8 liters and also has a float switch 36 disposed close to its bottom. When the level of fluid in the input container 14 is less than a predetermined level of perhaps 1 liter or less, the input pump 12 is disabled.

The 45 mm Hg pressure gauge 20 is connected to the output suction pump 30 so that the output suction pump 30 is enabled or energized when the input pressure is greater than about 45 mm Hg. Of course, the pressure may be different as determined by various clinical trials. The input pump 12 is connected to the 75 mm Hg pressure gauge 18, so that the input pump 12 is disabled when the input pressure exceeds 75 mm Hg. Of course, this value may also be changed depending upon clinical trials.

The pumps 12 and 30 may be operated by AC or DC power. If AC electricity is not available because of power outage or other reasons, a gravity and pressure valve arrangement may be employed.

The length of the concentric tubes is on the order of 36–48 inches. Its outer dimension is about ⅝ inches and its inner dimension is about ⅜ inches. The tubes may be made of flexible plastic to allow for flexibility and ease of cleaning and disinfecting. These may be available as either pre-sterilized and disposable, or reusable after proper sterilization. The ends of the tubes should preferably be rounded and free of sharp angles so as not to perforate the bowel wall of the patient.

In cases where the ileo-cecal has been damaged through disease or surgery, it may be necessary or desirable to incorporate inflatable doughnut-shaped balloons 40, 42 at the end of the tubes, as shown. The balloons are connected to an air line 44 embedded in the input tube, which air line 44 is connected to a balloon pump 46, of conventional design, for inflating and controlling the deflating of the balloons 40, 42.

A wire 48 encased in the input tube may also be provided which carries a low voltage current, for controlling ion flow and increasing osmotic effect of the filtrate solution. The wire 48 is connected to a DC voltage source 50, which is grounded to the patient by a skin electrode, for example.

Figure 2:
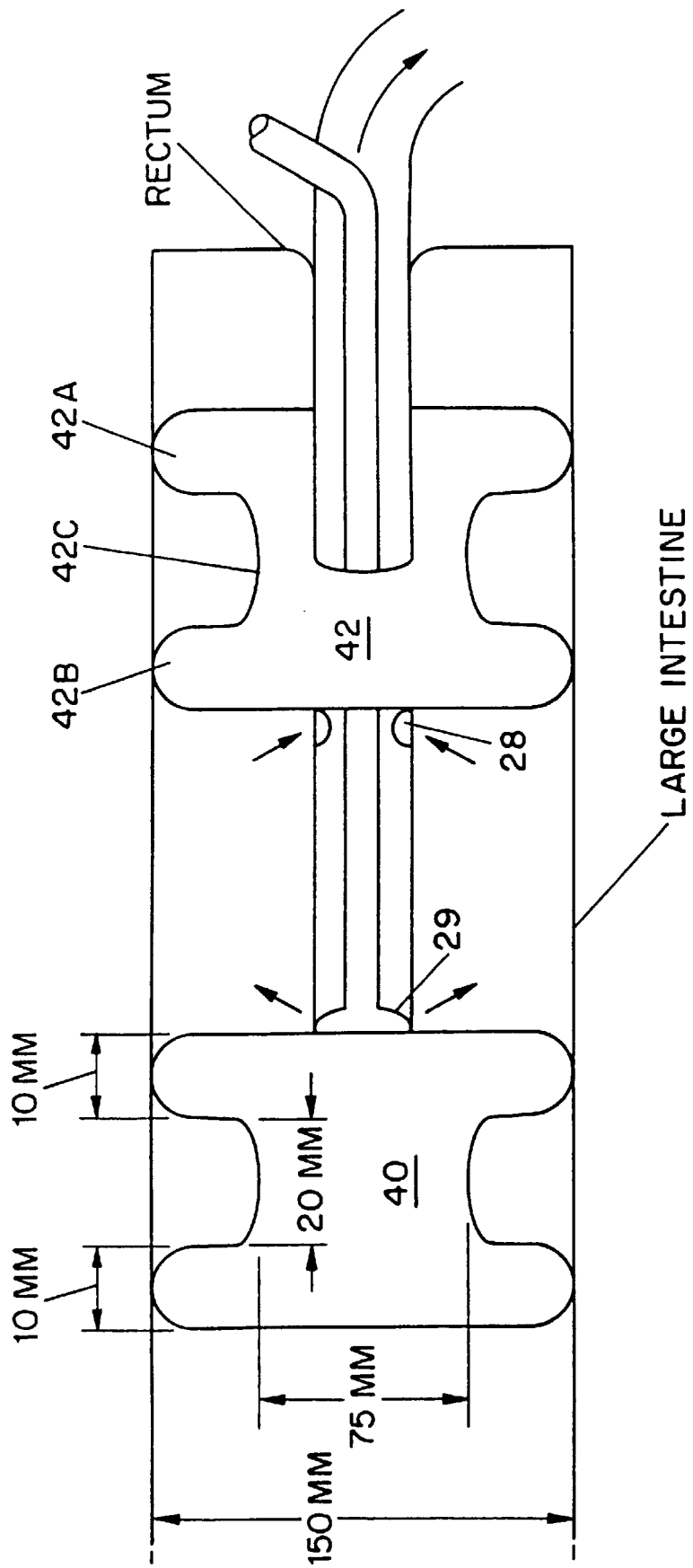
FIG. 2 is an elevational view of a balloon donut design for the system according to the invention.

FIG. 2 shows a balloon donut design having balloons 40, 42 particularly suited to limit movement from peristalsis, thereby assuring the sealing off of a segment of the large intestine in an area suitable for rapid diffusion. The cellular make-up of the approximately 25 cm of colon proximal to the rectum is stratified, leaving no available diffusible surface area. The balloon 42 is located preferably at least 25 cm from the rectum and is formed of two spaced donut portions 42A and 42B. Each donut portion is inflatable to a 150 mm maximum diameter. The inner or middle portion 42C is inflatable to maximum diameter of 75 mm. The width of the inner portion 42C is about 20 mm, and the width of the outer portions 42A, 42B are each about 10 mm, these dimensions being exemplary and not limiting. Balloon 40 is similarly arranged. Leaving a 20 mm gap (between the portions 42A, 42B) in which the myenteric plexus will not be activated by distention should eliminate/reduce peristalsis and thereby maintain ideal position of the sealed off segment in an area richly supplied with cells with great diffusion capability as well as greatly expanded surface area.

Figure 3:
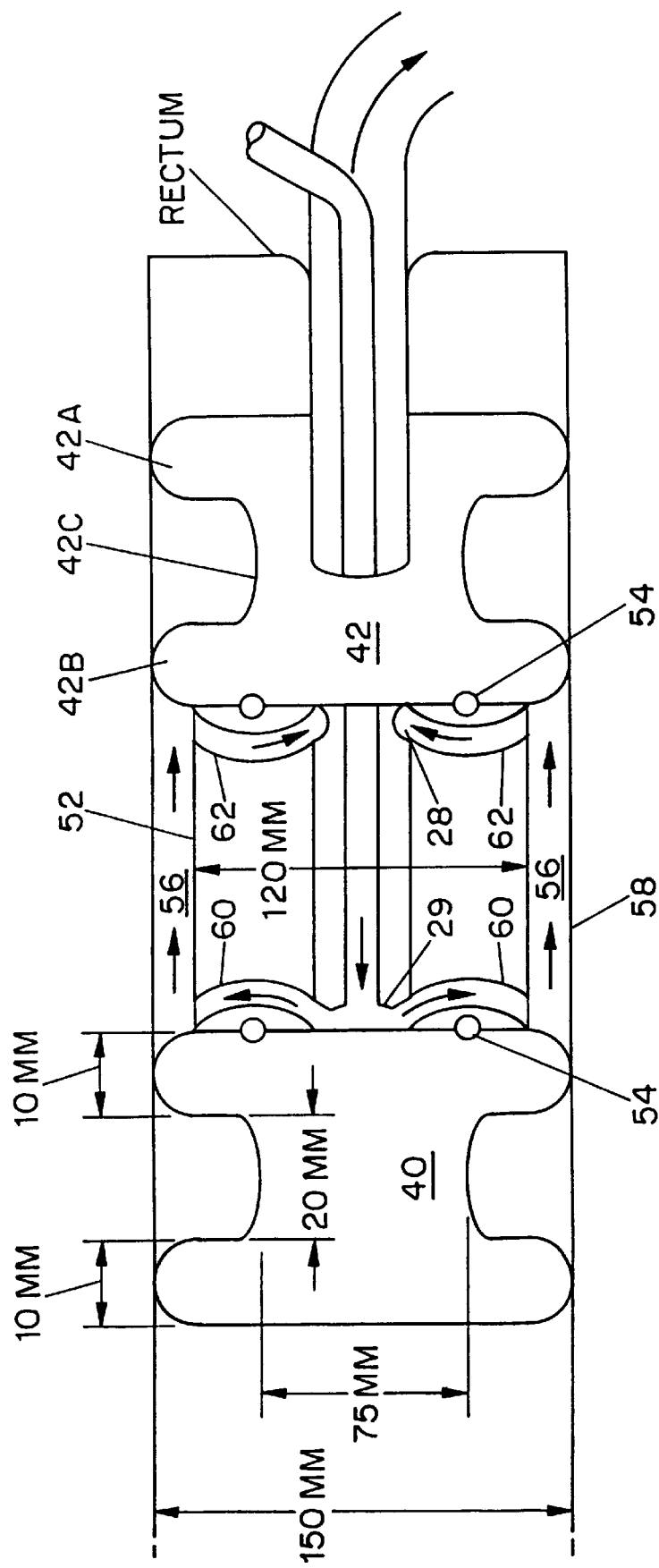
FIG. 3 is an elevational view of a balloon donut design having an inflatable central cylinder.

FIG. 3 shows a balloon donut design similar to that of FIG. 2, while also including an inflatable central balloon cylinder 52 disposed between donuts 40 and 42 and surrounding the input and output tubes 22, 24. The inflatable cylinder 52 is, during insertion and removal of the device, in a deflated condition like the donuts 40 and 42. The cylinder is in fluid communication with the donuts 40 and 42 through ports 54 and will thus inflate and deflate with the donuts 40 and 42. Actually, during inflation, donut 42 will inflate first, followed by cylinder 52, and then donut 40. The cylinder 52 insures maximal interface of the dialysate and the large intestine semi-permeable membrane 58 in the dialysis region 56 between the cylinder 52 and membrane 58. The dialysate will flow in the direction of the arrows through openings 29 at the distal end 26 of the input tube 22, through connecting input tubes 60 into the region 56, then through connecting output tubes 62 to openings 28 into the output tube 24.

The large intestine is a semi-permeable membrane allowing transport or diffusion or water soluble elements. The purpose of the filtrate solution according to the invention is to provide a vehicle in which undesirable elements or toxins may be removed from the serum of the large intestine without affecting the basic homeostatic mechanisms and important mineral and pH balances. The filtrate composition preferably consists of the following components:

TABLE A

| | |
|---|---|
| Sodium Chloride | 120 mEq/liter |
| Potassium Gluconate | 5.0 mEq/liter |
| Magnesium Citrate | 2.4 mEq/liter |
| Calcium Lactate | 18 mEq/liter |
| Ferrous Citrate | 220 mg./liter |
| Zinc Citrate | 205 mcg./liter |
| Vitamin C (Ascorbic Acid) | 400 mg./liter |
| Lemon bioflavinoids | 15 mg./liter |
| Rutin | 15 mg./liter |
| Hesperidin | 15 mg./liter |
| Acerola | 15 mg./liter |
| Niacin | 20 mg./liter |
| Casein (to achieve a filtrate osmolality of 450 mosm/kg) | |
| Sodium Bicarbonate (min. of 40 mEq/liter) and Glucoronic Acid to produce a highly buffered pH of about 7.38 pH. | |

The mineral constituents serve to maintain proper serum levels of the associated minerals. Niacin is provided for its vasodilator effect and the concomitant effect to increase blood supply to the area, thereby shorting time for serum filtration. Casein is provided to introduce a high molecular weight protein that is not available to transport through the membrane wall, i.e. to effect the osmotic pressure that will achieve diffusion of elements across the membrane into the filtrate. The filtrate is in a water base and is buffered preferably to a pH of about 7.38. It should of course be understood that the concentration values given may be adjusted or changed after clinical test. The make up of the components may be modified to adjust to individual, metabolic distortions or to sensitivities to the components of the patient.

The present invention provides another embodiment of a dialysis filtrate composition. The objective is to remove about 24 grams of urea daily. The dialysis filtrate composition has as its goals: (1) the re-establishment of proper electrolyte concentrations, (2) maintaining proper acid-base equilibrium, and (3) removal of nitrogenous and other associated waste. The dialysis filtrate composition according to this embodiment preferably comprises the following ingredients with the preferred values and ranges indicated:

TABLE B

| Electrolytes: | Sodium | 135 mmol/l, range | 134–147 mmol/l |
| --- | --- | --- | --- |
| | Potassium | 4 mmol/l, range | 3–5 mmol/l |
| | Magnesium | 1 mmol/l, range | 0.75–2.3 mmol/l |
| | Calcium | 2 mmol/l, range | 1–3.5 mmol/l |
| | Chloride | 105 mmol/l, range | 95–110 mmol/l |
| Buffer: | Bicarbonate | 37 mmol/l, range | 35–45 mmol/l |
| | Lactate | 8 mmol/l, range | 0–9 mmol/l |
| High Mol. weight Osmotic Agent: | | range 3–16% | |

The lactate could be reduced or eliminated, in which case it would preferably be replaced on almost a mmol/l per mmol/l basis by bicarbonate, which could then be increased up to 45 mmol/l if no lactate is used. The bicarbonate is an ideal physiological buffer. The lactate also serves as a buffer, and as a vasodilator.

The high molecular weight osmotic agent can be any medium weight (eg. about 16 k Daltons) to high molecular weight polymer, protein or amino acid, or combination thereof, that is non-irritating and not readily absorbed in the colonic mucosa. Such examples are maltodextrin (having a molecular weight of 16 k Daltons), and casein.

If necessary or desirable another vasodilator such as niacin in an amount of about 0.25 mg/l may be added to promote increased local/systemic vasodilation.

If necessary or desirable, an ingredient to promote increased ammonium binding may be added to lessen the time necessary for treatment. Such ingredient could be activated charcoal or other synthetic sorbent in an amount of about 15 g/l.

If necessary or desirable, an ingredient may be added to promote increased creatinine binding and removal, such as zirconium phosphate in an amount of about 2 g/l.

To increase the effective removal of cholesterol and triglycerides, the concentration of the osmotic agent can be increased to thereby increase the osmotic pressure, at only a slight increase in risk of irritation, which should be tolerable.

Through the use of the iontophoretic component, antigen/antibody complexes should be removable with or without addition of binding agents.

The present invention also provides an apparatus, method and composition for treating shock. The same apparatus and method described for dialysis could be adapted for treating shock. The composition would be more tailored to treating shock.

In treating shock the invention has three goals: (1) the correction of any electrolyte composition deviations, (2) the maintenance of proper acid-base equilibrium, and (3) rehydration as well as increased serum osmotic pressure to curtail capillary leakage. The shock treatment composition according to the invention preferably comprises the following ingredients:

| Electrolytes: | Sodium | 135 mmol/l, range | 134–147 mmol/l |
| --- | --- | --- | --- |
| | Potassium | 4 mmol/l, range | 3–5 mmol/l |
| | Magnesium | 1 mmol/l, range | 0.75–2.3 mmol/l |
| | Calcium | 2 mmol/l, range | 1–3.5 mmol/l |
| | Chloride | 105 mmol/l, range | 95–110 mmol/l |
| Buffer: | Bicarbonate | 37 mmol/l, range | 35–45 mmol/l |
| | Lactate | 8 mmol/l, range | 0–9 mmol/l |
| Rehydrating Agent: | | 3–6% by weight | |

The lactate could be reduced or eliminated, in which case it would preferably be replaced by bicarbonate, which could then be increased almost on a mmol/l per mmol/l basis with the amount of lactate reduced, or up to 45 mmol/l of bicarbonate if no lactate is used.

The rehydrating agent is preferably a non-irritating readily absorbed saccride disaccride, e.g. sorbitol, which would increase the serum osmotic pressure.

While all the above percentages and concentrations described are believed to be appropriate and efficacious, these values may be increased or decreased as the need arises or as may be dictated by clinical trials.

Although one or more preferred embodiments of the system, method and composition according to the present invention have been shown and described, it will be understood that numerous variations and modifications may be effected without departing from the true novel concept and spirit of the present invention. Accordingly, the present invention is not limited to the preferred embodiments disclosed, and is defined by the appended claims.

What is claimed:

1. A filtrate composition for use in dialysis via the colon, comprising:
   a vasodilator
   a high molecular weight protein being present in a sufficient amount to effect osmotic pressure to achieve diffusion of elements across the large intestine membrane into the filtrate and having a sufficient molecular weight such that it is not readily absorbed in the colonic mucosa; and
   mineral constituents for maintaining proper serum levels in the large intestine.

2. The composition according to claim 1, wherein the vasodilator is niacin.

3. The composition according to claim 1, wherein the high molecular weight protein is casein.

4. The composition according to claim 1, wherein the mineral constituents are selected from the group consisting of sodium chloride, potassium gluconate, magnesium citrate, calcium lactate, ferrous citrate and zinc citrate.

5. The composition according to claim 1, further comprising ascorbic acid.

6. The composition according to claim 1, further comprising lemon bioflavinoids.

7. The composition according to claim 1, further comprising rutin.

8. The composition according to claim 1, further comprising hesperidin.

9. The composition according to claim 1, further comprising acerola.

10. The composition according to claim 1, further comprising sodium bicarbonate and glucuronic acid to maintain a buffered pH of about 7.38 pH.

11. A filtrate composition for use in dialysis via the colon, comprising:
    electrolytes for establishing electrolyte concentrations;
    buffers for maintaining acid-base equilibrium; and
    a high molecular weight osmotic agent being present in a sufficient amount for removing nitrogenous waste, said agent having a sufficient molecular weight such that it is not readily absorbed in the colonic mucosa.

12. The composition according to claim 11, wherein the electrolytes are selected from the group consisting of sodium, potassium, magnesium, calcium and chloride.

13. The composition according to claim 11, wherein the buffers are selected from the group consisting of bicarbonate and lactate.

14. The composition according to claim 11, wherein the high molecular weight osmotic agent is selected from the group consisting of maltodextrin and casein.

15. The composition according to claim 11, further comprising a vasodilator.

16. The composition according to claim 11, further including an ammonium binding ingredient selected from the group consisting of activated charcoal and synthetic sorbents.

17. The composition according to claim 11, further including an ingredient to promote increased creatinine binding and removal.

18. The composition according to claim 17, wherein the ingredient is zirconium phosphate.

19. The composition according to claim 11, further including an iontophoretic component.

20. A filtrate composition for use in dialysis, comprising:

a vasodilator;

a high molecular weight protein to effect osmotic pressure to achieve diffusion of elements across the large intestine membrane into the filtrate;

mineral constituents for maintaining proper serum levels in the large intestine; and sodium bicarbonate and glucuronic acid to maintain a buffered pH of about 7.38 pH.

* * * * *